US00PP23399P2

(12) United States Plant Patent
Cain

(10) Patent No.: US PP23,399 P2
(45) Date of Patent: Feb. 19, 2013

(54) GRAPEVINE 'IFG SEVEN'

(50) Latin Name: ***Vitis* interspecific hybrid**
Varietal Denomination: IFG Seven

(75) Inventor: David Cain, Bakersfield, CA (US)

(73) Assignee: International Fruit Genetics LLC, Bakersfield, CA (US)

( * ) Notice: Subject to any disclaimer, the term of this patent is extended or adjusted under 35 U.S.C. 154(b) by 0 days.

(21) Appl. No.: 13/199,229

(22) Filed: Aug. 24, 2011

(51) Int. Cl.
*A01H 5/00* (2006.01)

(52) U.S. Cl. ..... Plt./207

(58) Field of Classification Search ..... Plt./207
See application file for complete search history.

*Primary Examiner* — Annette Para

(57) ABSTRACT

This invention is a new and distinct interspecific grapevine denominated 'IFG Seven'. 'IFG Seven' is characterized by producing large, firm, oval green seedless berries with a distinctive and unique flavor. The fruit ripen and are harvestable from mid to late August.

1 Drawing Sheet

Latin name of the genus and species claimed: *Vitis* interspecific hybrid.

Variety denomination: 'IFG Seven'.

BACKGROUND OF THE INVENTION

The new and distinct grapevine described and claimed herein originated from a hand pollinated cross of the A2674 selection (an unnamed interspecific *Vitis* selection received under contract from the University of Arkansas) and the Princess variety (non-patented) hybridized in May 2003. The abortive seed traces were subsequently embryo cultured and the resulting plant was planted in the field in April 2004. The present variety of grapevine was selected as a single plant in July 2005 and was first asexually propagated by hardwood cuttings in December 2005 near Delano, Kern County, Calif. The resulting propagules were planted during April 2006 near Delano, Kern County, Calif. and were found to reproduce true-to-type through at least two generations of asexual reproduction.

BRIEF SUMMARY OF THE INVENTION

The new grapevine 'IFG Seven' is characterized by producing large, oval green seedless berries with a distinctive flavor described as toffee or cotton candy. Typical commercial grape varieties are of the *vinifera* species and have a neutral flavor characterized mainly by sugar and acid with no strong aromatic component. Grape breeders have used several native American grape species to improve hardiness, disease and insect resistance as well as incorporate aromatic flavors into the *vinifera* species. Previously introduced interspecific varieties have had very limited commercial success due to small fruit size, large seed traces, slipskin texture or lack of firmness. The new grapevine 'IFG Seven' uniquely combines large firm seedless berries with a distinctive aromatic flavor. The vine is productive and can be pruned to short spurs. Berries ripen approximately mid-August in Delano Calif. Berries are light green in color but can amber when exposed to full sun and are moderately susceptible to bruising.

The new grapevine most closely resembles its pollen parent the Princess variety but can be distinguished from Princess by having slightly smaller, less cylindrical and more oval berries with a very strong aromatic flavor that the Princess variety lacks. 'IFG Seven' can be distinguished from its pollen parent, A2674 by its larger cluster size and its larger more oval berries which have much smaller seed remnants.

BRIEF DESCRIPTION OF THE FIGURE

The accompanying photographic illustration in FIG. 1 illustrates in full color 'IFG Seven'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Seven' plants grown in the vicinity of Delano, Kern County, Calif. during 2010, and is believed to apply to plants of the variety grown under similar conditions of soil and climate elsewhere:

VINE

General:

*Size*.—Large.
*Vigor*.—Vigorous.
*Density of foliage*.—Medium.
*Productivity*.—Productive.
*Root stock*.—Own root.

*Training method*.—Typically spur pruned leaving 2 bud spurs.

Trunk:

*Trunk diameter of 4-year-old vines at 30 cm above the soil line*.—4.9 cm.

*Shape*.—Medium — Slender.

*Straps*.—Short — Split.

*Surface texture*.—Medium.

*Inner bark color*.—Can be any of the following colors; Grayed-purple; 184A and B, and 185A.

SHOOTS

Young shoot:

*Form of tip*.—Fully opened.

*Distribution of anthocyanin coloration of tip*.—Piping (striped).

*Intensity of anthocyanin coloration of tip*.—Very weak.

*Density of prostrate hairs of tip*.—Dense. Density of erect hairs of tip — Absent.

*Color*.—Can be any of the following colors; Green; 146A and B, and N144C, and 144A, and Greyed-purple; 184A and B, and 185A.

Woody shoot (mature canes):

*Shape*.—Medium — Slender.

*Internode length*.—Short — Medium; About 8.3 cm.

*Width at node*.—About 0.9 cm.

*Cross section*.—Elliptic.

*Surface*.—Striate — Ribbed.

*Main color*.—Can be any of the following colors; Dark brown — Reddish brown; 166D, and 175A.

*Density of erect hairs of nodes*.—None or very sparse.

*Density of erect hairs on internodes*.—None.

*Growth of axillary shoots at full bloom*.—Medium; Approximately 28.1 cm.

Flowering shoot:

*Vigor during flowering*.—Medium.

*Attitude during flowering on shoots not tied*.—Erect — Semi-erect.

*Color*.—Dorsal side of internodes — Green with Red stripes.

*Color*.—Ventral side of internodes — Green with Red stripes.

*Color*.—Dorsal side of nodes — Green with Red stripes.

*Color*.—Ventral side of nodes — Green with Red stripes.

*Density of prostrate hairs of nodes*.—Very sparse.

*Density of erect hairs of nodes*.—None.

*Density of prostrate hairs on internode*.—Very sparse.

*Density of erect hairs on internode*.—None.

*Anthocyanin coloration of buds*.—Absent.

Tendrils:

*Distribution on the shoot* (*at full flowering*).—Discontinuous.

*Length of tendril*.—Long; About 22.1 cm.

*Thickness*.—Medium.

*Color*.—Can be either of the following colors; Yellow-green; 144A and B.

*Form*.—Bifurcated — Trifurcated — Quadfurcated.

*Number of consecutive tendrils*.—2.

LEAVES

Young leaves:

*Color of upper surface of first four distal unfolded leaves*.—Can be either of the following colors; Green; 146A and B.

*Average intensity of anthocyanin coloration of six distal leaves prior to flowering*.—Absent or very weak.

*Density of prostrate hairs between veins* (*lower surface*).—Very sparse.

*Density of prostrate hairs on veins* (*lower surface*).—Sparse — Medium.

*Density of erect hairs between veins* (*lower surface*).—Absent.

*Density of erect hairs on veins* (*lower surface*).—Sparse —Medium.

Mature leaves:

*Average length*.—About 14.3 cm.

*Average width*.—About 18.5 cm.

*Mature leaf size*.—Medium — Large.

*Shape of blade*.—Wedge-shaped.

*Number of lobes*.—5.

*Anthocyanin coloration of main veins on upper side of blade*.—Absent — Very weak.

*Mature leaf profile*.—Flat.

*Blistering surface of blade upper surface*.—Weak — Medium.

*Leaf blade tip*.—In the plane of the leaf.

*Undulation of margin*.—Slight.

*Thickness*.—Thick.

*Undulation of blade between main and lateral veins*.—Absent.

*Shape of teeth*.—Mixture of both side's straight and both sides convex.

*Length of teeth*.—Medium.

*Ratio length/width of teeth*.—Small.

*Shape of upper lateral sinuses*.—Open.

*Depth of upper lateral sinuses*.—Shallow.

*General shape petiole sinus*.—Half open — Slightly open.

*Shape of base of upper leaf sinuses*.—U-shaped.

*Tooth at petiole sinus*.—Absent.

*Density of prostrate hairs between veins on lower surface of blade*.—Very sparse.

*Density if erect hairs between veins on lower surface of blade*.—Very sparse.

*Density of prostrate hairs on main veins on lower surface of blade*.—Sparse.

*Density of erect hairs on main veins on lower surface of blade*.—Medium.

*Density of prostrate hairs on main veins on upper surface of blade*.—Sparse.

*Density of erect hairs on main veins on upper surface of blade*.—None.

*Autumn coloration of leaves*.—Leaves can be a single color or combination of colors, in a mottled pattern or on the edges of the leaves; Yellow; 13B, and 10A and B, and Yellow — green; 151A.

Upper surface:

*Color*.—Can be any of the following colors; Green; 147B, and 146A and B.

*Anthocyanin coloration of main veins*.—Absent — Very weak.

*Surface appearance*.—Semi-glossy.

*Blistering surface of blade*.—Weak.

Lower surface:

*Color*.—Can be any of the following colors; Green; 146A and B and C.

*Anthocyanin coloration of main veins* (*lower surface*).—Absent.

*Glossiness*.—Weak.

*Surface texture*.—Rugose.

*Surface appearance*.—Dull.

Petiole:

*Length*.—About 11.5 cm.

*Length of petiole compared to middle vein*.—Slightly shorter.

*Density of prostrate hairs on petiole*.—Sparse.

*Density of erect hairs on petiole*.—None.

Buds:

*Bud fruitfulness*.—Basal; Mostly fruitful.

*Position of first fruitful shoot on previous season cane*.—$1^{st}$ to $2^{nd}$ node.

*Time of bud burst*.—Late; Mar. 20, 2010.

FLOWERS

General:

*Flower sex*.—Hermaphrodite.

*Length of first inflorescence*.—Medium; About 17.9 cm long by 14.8 cm wide.

*Position of first flowering and fruiting node*.—$3^{rd}$-$4^{th}$ (current season growth).

*Number of inflorescence per flowering shoot*.—1.1 to 2.

*Time of bloom*.—Medium to Late as compared with similar varieties in the growing area of Delano, Calif.

*Date of full bloom*.—May 20, 2010.

FRUIT

General:

*Ripening period*.—Late; Approximately Sep. 6, 2010.

*Use*.—Fresh market.

*Keeping quality*.—Good.

*Resistance to*.—Insects: Average typical of *Vitis vinifera* species. Diseases: Average typical of *Vitis vinifera* species.

*Refractometer test*.—Solid-sugar: About 19.2 Brix.

*Brix/acid*.—About 68.6.

*Titratable acidity*.—About 0.28.

*Juice pH*.—About 4.14.

Cluster:

*Mature cluster length* (*peduncle excluded*).—About 24.1 cm.

*Mature cluster width*.—About 20.4 cm.

*Mature cluster weight*.—About 1261 g.

*Bunch density*.—Loose — Medium.

*Number of berries*.—About 157.

*Form*.—Circular — Conical.

Peduncle:

*Lignification of peduncle*.—Weak.

*Length of peduncle*.—Medium. Approximately 2.7 cm.

Berry:

*Uniformity of size*.—Uniform.

*Single berry weight*.—About 9.7 g natural.

*Shape*.—Elliptic — Obtuse ovate.

*Seeds*.—Contains small rudimentary seed traces.

*Cross section*.—Circular.

*Berry dimensions*.—Longitudinal axis: About 28.3 mm. Horizontal axis: About 22.8 mm.

*Berry firmness*.—Soft — Medium.

*Particular flavor*.—Similar to Toffee or Cotton Candy having a hint of *Vitis riparia* flavor.

*Bloom* (*cuticular wax*).—Very weak.

*Berry separation from pedicel*.—Medium.

*Skin color* (*without bloom*).—Yellow — Green; single berries can be a range of colors, depending on sun exposure and individual berry maturity; 151D, and 144D, and 153C and D.

Skin:

*Thickness*.—Medium.

*Texture*.—Medium.

*Reticulation*.—Absent.

*Tenacity*.—Tenacious to flesh.

What is claimed:

1. A new and distinct variety of grapevine as herein illustrated and described.

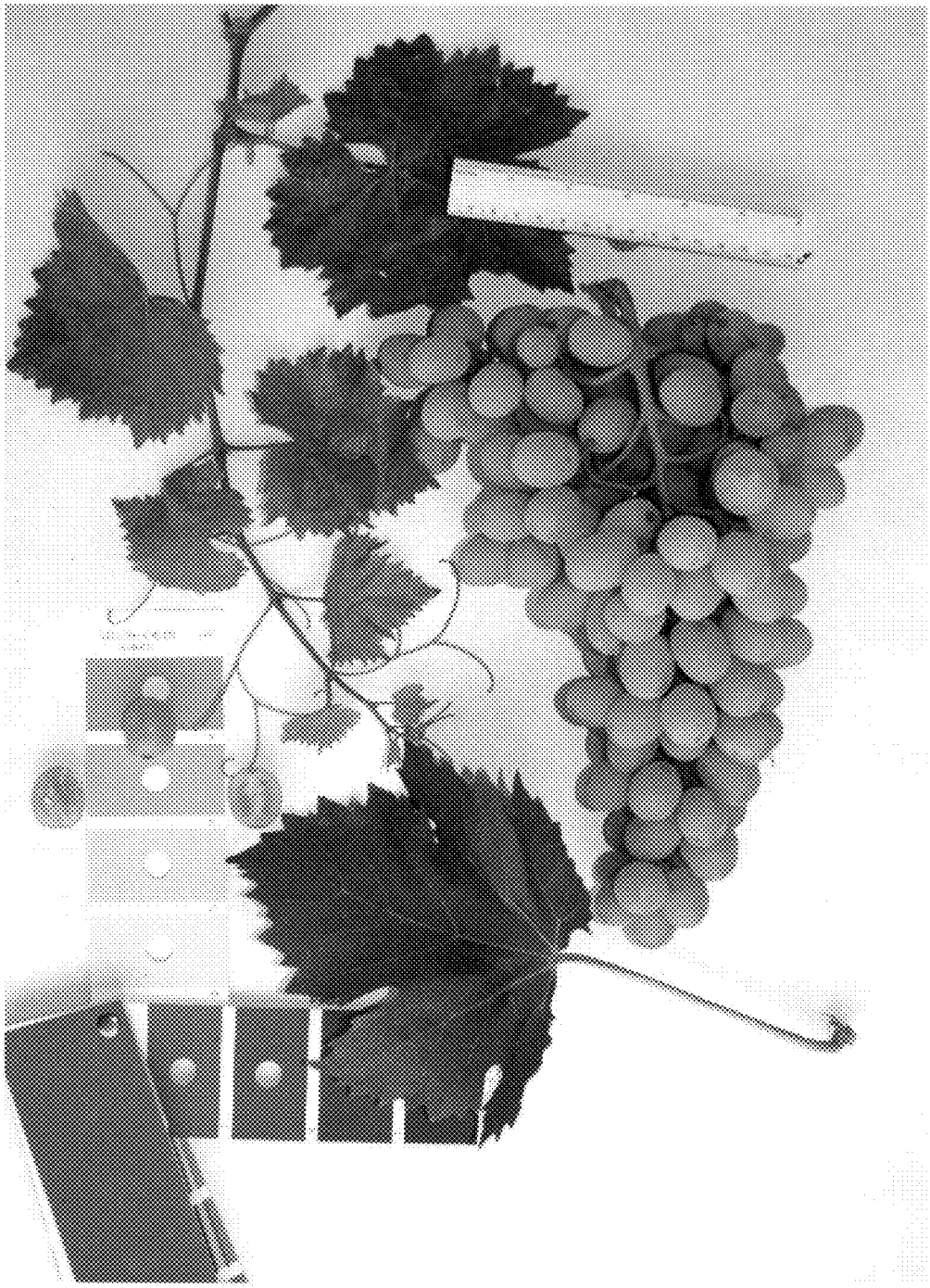

* * * * *